United States Patent
Lou et al.

(10) Patent No.: US 10,105,110 B2
(45) Date of Patent: Oct. 23, 2018

(54) SELECTING SCANNING VOLTAGES FOR DUAL ENERGY CT SCANNING

(71) Applicant: SHENYANG NEUSOFT MEDICAL SYSTEMS CO., LTD., Shenyang (CN)

(72) Inventors: Shanshan Lou, Shenyang (CN); Ling Pang, Shenyang (CN); Mingjie Zhang, Shenyang (CN)

(73) Assignee: Shenyang Neusoft Medical Systems Co., Ltd., Shenyang (CN)

( * ) Notice: Subject to any disclaimer, the term of this patent is extended or adjusted under 35 U.S.C. 154(b) by 402 days.

(21) Appl. No.: 14/975,125

(22) Filed: Dec. 18, 2015

(65) Prior Publication Data

US 2016/0183355 A1 Jun. 23, 2016

(30) Foreign Application Priority Data

Dec. 18, 2014 (CN) .......................... 2014 1 0802373

(51) Int. Cl.
| | |
|---|---|
| *H05G 1/00* | (2006.01) |
| *A61B 6/03* | (2006.01) |
| *A61B 6/00* | (2006.01) |
| *H05G 1/58* | (2006.01) |

(52) U.S. Cl.
CPC .............. *A61B 6/032* (2013.01); *A61B 6/482* (2013.01); *A61B 6/54* (2013.01); *H05G 1/58* (2013.01)

(58) Field of Classification Search
CPC ...... H05G 1/58; H05G 1/32; G06T 2211/408; G06T 11/005; A61B 6/542; A61B 6/032; A61B 6/488; A61B 6/545; A61B 6/583; A61B 6/482; A61B 6/544; A61B 6/405; A61B 6/06; A61B 6/5258; A61B 5/4869; A61B 6/027; A61B 6/4241; A61B 6/467; A61B 6/50; A61B 6/505; A61B 6/5205; A61B 6/037; A61B 6/4035; A61B 6/541; A61B 6/4007; A61B 6/4233; A61B 6/585; A61B 6/481; A61B 6/5217; A61B 6/54; A61B 6/03; A61B 6/502; A61B 6/4014;

(Continued)

(56) References Cited

U.S. PATENT DOCUMENTS

| | | |
|---|---|---|
| 4,541,106 A | 9/1985 | Belanger et al. |
| 2009/0207966 A1 | 8/2009 | Shkumat et al. |

(Continued)

FOREIGN PATENT DOCUMENTS

| | | |
|---|---|---|
| CN | 101726502 A | 6/2010 |
| CN | 101772324 A | 7/2010 |

(Continued)

*Primary Examiner* — Irakli Kiknadze
(74) *Attorney, Agent, or Firm* — McCoy Russell LLP

(57) ABSTRACT

A method and apparatus for selecting high and low energy scanning voltages for a dual energy CT scanner are provided. The method may comprise: setting a criterion of selection for selecting high and low energy scanning voltages; generating combinations of high and low energy scanning voltages according to all scanning voltages supported by a dual energy CT scanner, wherein each of the combinations may comprise a high energy scanning voltage and a low energy scanning voltage; and selecting a combination of high and low energy scanning voltages from the generated combinations of high and low energy scanning voltages based on the criterion of selection.

11 Claims, 4 Drawing Sheets

(58) Field of Classification Search
CPC ......... A61B 6/025; A61B 6/4042; A61B 6/40;
A61B 6/52
USPC ............................................. 378/4, 5, 19, 62
See application file for complete search history.

(56) References Cited

U.S. PATENT DOCUMENTS

| | | | |
|---|---|---|---|
| 2010/0303196 A1* | 12/2010 | Zou .................. | A61B 6/032 378/5 |
| 2012/0076258 A1 | 3/2012 | Chandra et al. | |
| 2014/0185758 A1 | 7/2014 | Kang et al. | |
| 2014/0321603 A1* | 10/2014 | Taguchi ............. | A61B 6/032 378/5 |

FOREIGN PATENT DOCUMENTS

| | | | |
|---|---|---|---|
| CN | 102076263 A | 5/2011 | |
| CN | 103822929 A | 5/2014 | |
| CN | 103892859 A | 7/2014 | |
| CN | 103913779 A | 7/2014 | |
| DE | 102012217569 A1 | 3/2014 | |
| JP | 2011167467 A | 9/2011 | |
| JP | 2013005854 A | 1/2013 | |

\* cited by examiner

SELECTING SCANNING VOLTAGES FOR DUAL ENERGY CT SCANNING

CROSS-REFERENCE TO RELATED APPLICATIONS

The present application claims priority to Chinese Patent Application No. 201410802373.0, filed on Dec. 18, 2014, the entire contents of which are hereby incorporated by reference for all purposes.

BACKGROUND

The present disclosure relates to the field of medical equipment, particularly to a method and apparatus for selecting scanning voltages of a dual energy Computed Tomography (CT) scanning.

Compared to single energy CT scanning, dual energy CT scanning typically functions better in distinguishing different materials.

For example, under the scanning voltage of 120 kV, the difference between the CT values of bone and iodine is relatively small. However, when under the scanning voltage of 80 kV, the difference is relatively large. Further analysis shows that under the scanning voltage of 70 kV or below, the difference between bone and iodine is even larger. On the other hand, as the scanning voltage is decreased, due to limitations of scanning capability of the system, noise in the image may grow larger and thus, may degrade the quality of the image.

Therefore, it may be desirable to develop a method of automatically selecting an optimal combination of high and low energy scanning voltages to guarantee the distinction of materials and image quality.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, MRI, digital X-ray machines, Ultrasound, PET (Positron Emission Tomography), Linear Accelerators, and Biochemistry Analysers. Currently, NMS' products are exported to over 60 countries and regions around the globe, serving more than 5,000 renowned customers. NMS'latest successful developments, such as the 128 Multi-Slice CT Scanner System, Superconducting MRI, Linear Accelerator, and PET products, have led China to become a global high-end medical equipment producer. As an integrated supplier with extensive experience in large medical equipment, NMS is committed to the study of avoiding secondary potential harm caused by excessive X-ray irradiation to the subject during the CT scanning process.

BRIEF DESCRIPTION OF DRAWINGS

Features of the present disclosure are illustrated by way of example and not limited in the following figure(s), in which like numerals indicate like elements, in which.

DETAILED DESCRIPTION

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

In a general dual energy CT scanning process, a high energy scanning voltage (usually 140 kV) and a low energy scanning voltage (usually 80 kV) may have been preset to conduct scanning. Although this combination of high and low energy scanning voltages (i.e., 140 kV/80 kV) may be widely used, it may not necessarily be the optimal combination in all instances.

Figure 1:
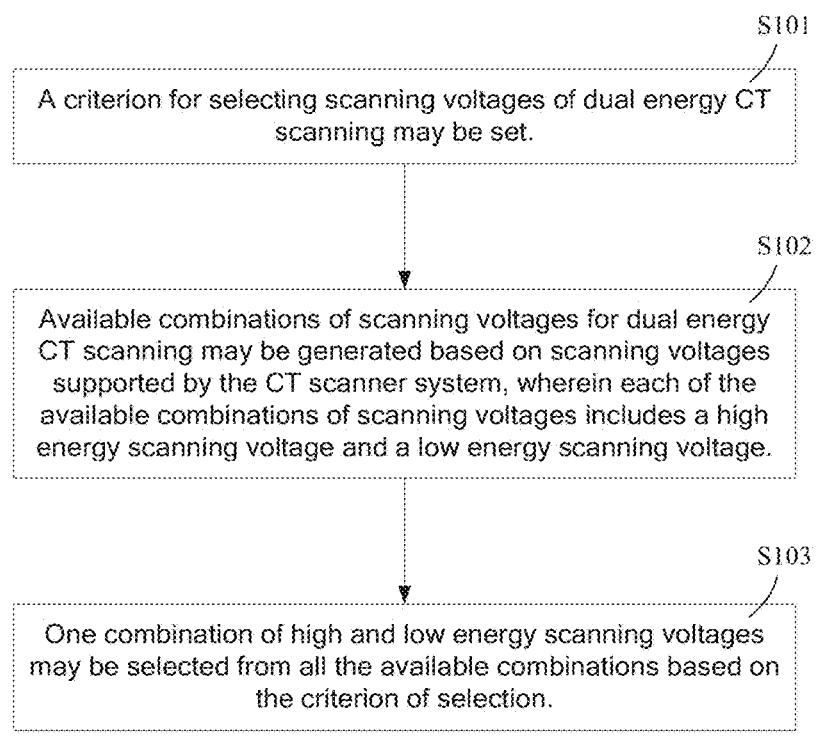
FIG. 1 is a flowchart illustrating a process for selecting scanning voltages for dual energy CT scanning according to an example of the present disclosure.

FIG. 1 is a flowchart illustrating a method for selecting high and low energy scanning voltages of dual energy CT scanning according to an example of the present disclosure. As shown in FIG. 1, the process may include blocks S101-S103.

At block S101, a criterion for selecting scanning voltages of dual energy CT scanning may be set.

The criterion of selection in block S101 may be varied according to the model of the CT scanner system and application scenarios thereof, etc. For example, the criterion of selection may be any one selected from the following five: a degree of contrast of a to-be-scanned material; a degree of contrast of a to-be-scanned material with a constraint of noise index; a degree of contrast of a to-be-scanned material with a constraint of noise and dose; a degree of contrast of spectrums of scanning voltages of dual energy CT scanning; and a degree of contrast of spectrums of scanning voltages of dual energy CT scanning with a constraint of dose.

At block S102, available combinations of scanning voltages of dual energy CT scanning may be generated based on scanning voltages supported by the CT scanner system, wherein each of the available combinations of scanning voltages includes a high energy scanning voltage and a low energy scanning voltage.

Usually, the scanning voltages supported by a CT scanner system may include multiple high energy scanning voltages and multiple low energy scanning voltages. Thus, all the scanning voltages supported by the CT scanner system and satisfying the image quality may be divided into a set of low energy scanning voltages and a set of high energy scanning voltages. Then, a low energy scanning voltage and a high energy scanning voltage are selected from each of the two sets respectively to form a combination of high and low energy scanning voltages. As to the term of "image quality", the present disclosure makes no specific definitions on this term, which may be defined, set or configured according to practical application scenarios discussed herein.

At block S103, one combination of high and low energy scanning voltages may be selected from all the available combinations based on the criterion of selection.

According to an example, a proper calculation may be performed on each of the possible combinations generated in block S102 according to the criterion of selection set in block S101, and an optimal combination of high and low energy scanning voltages may be selected from all the possible combinations.

In a conventional method of dual energy CT scanning, a high energy scanning voltage is fixedly set as 140 kV and a low energy scanning voltage is fixedly set as 80 kV. In contrast, the present disclosure provides a method for selecting scanning voltages of dual energy CT scanning, which may include setting a criterion of selection according to the practical conditions of the CT scanner system and selecting an optimal combination of high and low energy scanning voltages as the scanning voltages for the CT scanner system from all the possible combinations satisfying the criterion of selection. Using the method of the present disclosure, the quality of a scanned image may be significantly improved.

The processes of selecting an optimal combination of high and low energy scanning voltages based on different criteria are described in detail below.

1. The degree of contrast of a to-be-scanned material is regarded in one example as the criterion of selection.

When taking the degree of contrast of a to-be-scanned material as the criterion of selection, a combination having the greatest absolute value of degree of contrast of two to-be-scanned materials $DE_{contrast}$ may be selected as an optimal combination of high and low energy scanning voltages.

According to an example, $DE_{contrast}$ may be calculated through the following formula:

$$DE_{contrast} = DE_{ratio\_material1} - DE_{ratio\_material2};$$

$$DE_{ratio} = \frac{CT_{highKV} - CT_{highKV\_ref}}{CT_{lowKV} - CT_{lowKV\_ref}};$$

where, $DE_{ratio}$ represents a ratio of CT values of a to-be-scanned material under high and low energy scanning voltages (the ratio is referred to as "high/low ratio" hereafter for simplicity), $DE_{ratio\_material1}$ represents a high/low ratio of a first to-be-scanned material, $DE_{ratio\_material2}$ represents a high/low ratio of a second to-be-scanned material;

$CT_{lowKV}$ and $CT_{highKV}$ represent CT values of a to-be-scanned material under low and high energy scanning voltages respectively;

$CT_{lowKV\_ref}$ represents a CT value of a preset reference material under a low energy scanning voltage, $CT_{highKV\_ref}$ represents a CT value of the preset reference material under a high energy scanning voltage;

$DE_{ratio}$ may then be acquired through experiments or calculations in advance.

It should be noted that $CT_{highKV\_ref}$ and $CT_{lowKV\_ref}$ may be equal or not equal, e.g., $CT_{highKV\_ref}$ and $CT_{lowKV\_ref}$ both may be 40. A larger absolute value of $DE_{contrast}$ may indicate a better degree of contrast, and if it is 0, it may indicate that the two different to-be-scanned materials may not be distinguished from each other. In one embodiment, $DE_{ratio}$ may be acquired through experiments. For example, a material to-be-scanned may be selected as well as corresponding high and low energy scanning voltages, and then $DE_{ratio}$ may be acquired through proper calculation on the scanned CT values under corresponding high and low energy scanning voltages.

The following table, Table 1, illustrates CT values measured under 80 KV/100 KV/120 KV/140 kV with respect to iodine solutions of different concentrations (iodine solution is a commonly used contrast medium in current clinical CT scanning methods). Table 2 illustrates CT values under 80 KV/100 KV/120 KV/140 kV with respect to multiple types of material including cort bone, CB2 30%, etc. The following table, Table 3, and a subsequent table, Table 4, illustrate values of $DE_{ratio}$ calculated based on the information provided in Table 1 and Table 2 under 80 kV and 140 kV as examples, respectively. An additional table, Table 5, illustrates values of $DE_{contrast}$ calculated based on the materials in Table 4 with respect to concentration 4 (C4) in Table 3.

As appreciated by those skilled in the art, the above experiments may be applied to other materials under all the possible scanning voltages supported by the CT scanning system in order to acquire values of $DE_{contrast}$ of those other materials under said scanning voltages.

TABLE 1

Variations of CT values of iodine solutions of different concentrations under the same dose

|       | C1     | C2     | C3     | C4    | C5    | C6    | C7    | C8    | C9    | C10   | C11  |
|-------|--------|--------|--------|-------|-------|-------|-------|-------|-------|-------|------|
| 80 kv | 1563.2 | 1264.4 | 1101.6 | 944.5 | 767.6 | 628   | 525   | 411.7 | 330.7 | 225.9 | 142  |
| 100 kv| 1227.7 | 994.4  | 866.8  | 743.4 | 604.2 | 493.9 | 412.5 | 322.7 | 258.4 | 175   | 108  |
| 120 kv| 1022.1 | 828.6  | 722.6  | 619.6 | 503.3 | 411.1 | 343   | 267.5 | 213.7 | 143.3 | 87   |
| 140 kv| 883.3  | 716.1  | 623.7  | 534.6 | 433.5 | 352.9 | 293.6 | 227.9 | 180.9 | 119.5 | 70.1 |

Annotation: The letter "C" represents "concentration" for abbreviation purposes.

It may be seen in Table 1 that the concentrations are decreasing from left to right.

TABLE 2

Variations of CT values of scanned phantoms made of different materials under the same dose

|        | cort bone | CB2 30% | CB2 50% | B-200 | Inner Bone | brain | Liver |
|--------|-----------|---------|---------|-------|------------|-------|-------|
| 80 kv  | 1590      | 560     | 1041    | 304   | 284        | 6     | 72    |
| 100 kv | 1323      | 478     | 870     | 248   | 229        | 19    | 70    |
| 120 kv | 1143      | 418     | 755     | 209   | 192        | 24    | 65    |
| 140 kv | 1032      | 380     | 681     | 186   | 168        | 27    | 61    | constraint of noise index $DE_{CNR}$ may be selected as an optimal combination of high and low energy scanning voltages.

According to an example, $DE_{CNR}$ may be calculated through an equation as follows:

$$DE_{CNR} = \frac{DE_{contrast}}{Noise};$$

where, Noise represents a known quantity, which is a preset noise index.

TABLE 3

Variations of $DE_{ratio}$ values of iodine solutions of different concentrations

|              | C1     | C2     | C3     | C4     | C5     | C6     | C7     | C8     | C9     | C10    | C11    |
|--------------|--------|--------|--------|--------|--------|--------|--------|--------|--------|--------|--------|
| 80 kv        | 1563.2 | 1264.4 | 1101.6 | 944.5  | 767.6  | 628    | 525    | 411.7  | 330.7  | 225.9  | 142    |
| 140 kv       | 883.3  | 716.1  | 623.7  | 534.6  | 433.5  | 352.9  | 293.6  | 227.9  | 180.9  | 119.5  | 70.1   |
| $DE_{ratio}$ | 0.5536 | 0.5522 | 0.5498 | 0.5468 | 0.5408 | 0.5321 | 0.5229 | 0.5055 | 0.4847 | 0.4276 | 0.2951 |

Annotation: The letter "C" represents "concentration" for abbreviation purposes.

TABLE 4

Variations of $DE_{ratio}$ values of different materials

|              | cort bone | CB2 30% | CB2 50% | B-200  | Inner Bone | brain  | Liver  |
|--------------|-----------|---------|---------|--------|------------|--------|--------|
| 80 kv        | 1590      | 560     | 1041    | 304    | 284        | 6      | 72     |
| 140 kv       | 1032      | 380     | 681     | 186    | 168        | 27     | 61     |
| $DE_{ratio}$ | 0.6400    | 0.6538  | 0.6404  | 0.5530 | 0.5246     | 0.3824 | 0.6563 |

TABLE 5

Variations of $DE_{contrast}$ values of the materials in Table 4 with respect to C4 in Table 3

|                 | cort bone | CB2 30% | CB2 50% | B-200  | Inner Bone | brain  | Liver  |
|-----------------|-----------|---------|---------|--------|------------|--------|--------|
| $DE_{ratio}$    | 0.6400    | 0.6538  | 0.6404  | 0.5530 | 0.5246     | 0.3824 | 0.6563 |
| $DE_{contrast}$ | 0.0932    | 0.1070  | 0.0936  | 0.0062 | 0.0222     | 0.1644 | 0.1095 |

2. The degree of contrast of a to-be-scanned material with a constraint of noise index may be regarded in one example as the criterion of selection.

When taking the degree of contrast of a to-be-scanned material with a constraint of noise index as the criterion of selection, the combination having the greatest absolute value of degree of contrast of the material to-be-scanned with 3. The degree of contrast of a to-be-scanned material with constraints of noise and dose is regarded in one example as the criterion of selection.

When taking the degree of contrast of a to-be-scanned material with constraints of noise and dose as the criterion of selection, the combination having the greatest absolute value of degree of contrast of the material to-be-scanned with constraints of noise and noise $DE_{CNRD}$ may be selected as an optimal combination of high and low energy scanning voltages.

According to an example, $DE_{CNRD}$ may be calculated through an equation as follows:

$$DE_{CNRD} = \frac{DE_{contrast}}{\text{Noise} * CTDI};$$

where, CTDI represents the sum of the scanning dose under a high energy scanning voltage and the scanning dose under a low energy scanning voltage, which may be acquired through calculation in advance;

Noise may be a known quantity, which may be a preset noise index;

$DE_{contrast}$ represents the degree of contrast of a to-be-scanned material.

4. The degree of contrast of spectrums of high and low energy scanning voltages is regarded in one example as the criterion of selection.

When taking the degree of contrast of spectrums of high and low energy scanning voltages as the criterion of selection, the process for selecting a optimal combination from all possible combinations of high and low energy scanning voltages may include:

acquiring an overlapping area $DE_{Area}$ of a spectrum corresponding to a low energy scanning voltage and another spectrum corresponding to a high energy scanning voltage of each combination, where a smaller value of the overlapping area $DE_{Area}$ may indicate a better degree of contrast of the to-be-scanned material;

selecting all the combinations of high and low energy scanning voltages having an overlapping area less than a preset value to form a candidate set, where the value $DE_{Area}$ being less than a preset value should be understood as a minimum criterion for a to-be-scanned material to be differentiated; and selecting a combination corresponding to a minimum overlapping area from a candidate set as an optimal combination of high and low energy scanning voltages.

Figure 2:
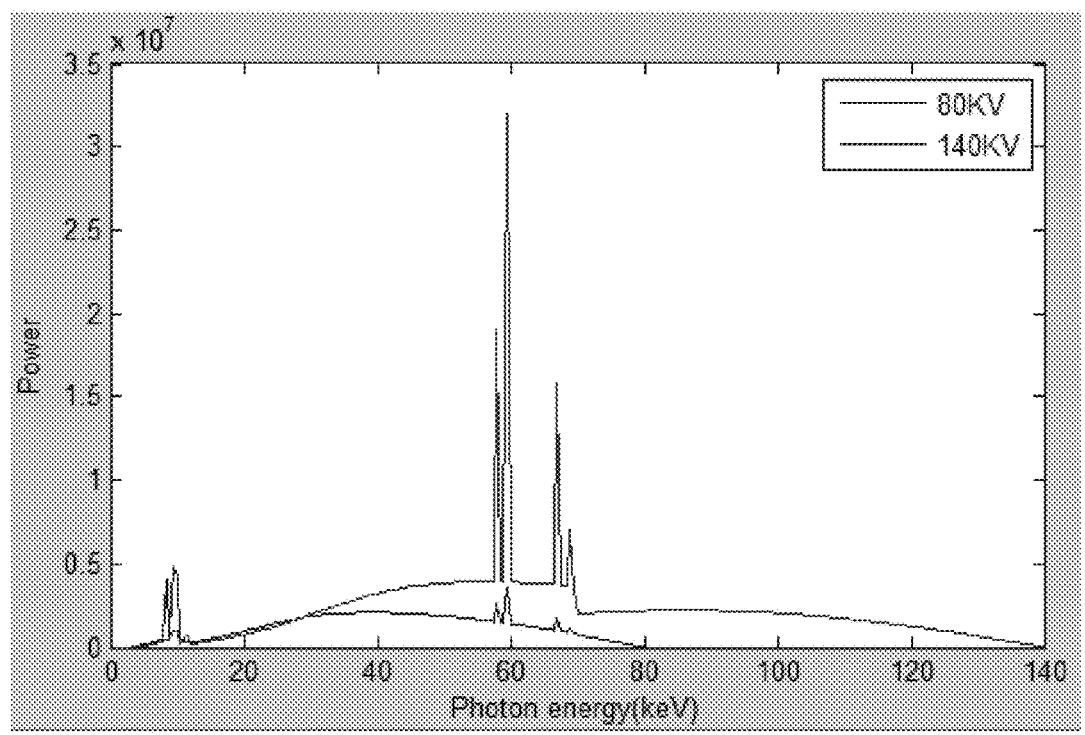
FIG. 2 is a spectral curve graph for 80 kV/140 kV according to an example of the present disclosure.

In practice, the spectrums of high and low energy scanning voltages may be derived and calculated through spectrum simulation software. Many general spectrum simulation software programs are known, such as Spectrum. FIG. 2 illustrates overlapping area of spectrums of 80 kV and 140 kV derived and calculated through spectrum simulation software. Those skilled in the art may sequentially calculate the overlapping area of the spectrums of any two scanning voltages selected from all the possible scanning voltages supported by a CT system.

5. The degree of contrast of spectrums of high and low energy scanning voltages with a constraint of dose is regarded in one example as the criterion of selection.

When taking the degree of contrast of spectrums of high and low energy scanning voltages with a constraint of dose as the criterion of selection, a process for selecting the optimal combination from all possible combinations according to the criterion of selection may include:

acquiring an overlapping area $DE_{Area}$ of a spectrum corresponding to a low energy scanning voltage and another spectrum corresponding to a high energy scanning voltage of each of the combinations;

collecting all the combinations having an overlapping area less than a preset value to form a candidate set; and selecting a combination corresponding to a minimum scanning dose from the candidate set as an optimal combination of high and low energy scanning voltages.

This criterion of selection may be different from the criterion of selection of 4 in that the criterion of selection of 4 may be to select the combination corresponding to the minimum overlapping area as an optimal combination from all the available combinations of high and low energy scanning voltages, while this criterion of selection may serve to select the combination corresponding to a minimum scanning dose as an optimal combination from all the available combinations of high and low energy scanning voltages.

It should be noted that other criterion of selection may be used according to the model of a CT scanner system and application scenarios, etc. The above-described criteria are only five typical criteria of selection.

A process of generating available combinations of high and low energy scanning voltages from all the scanning voltages supported by a CT scanner system may include the following.

First, all the scanning voltages supported by a CT scanner system and satisfying an image quality requirement may be classified into a set of low energy scanning voltages and a set of high energy scanning voltages, and then a low energy scanning voltage and a high energy scanning voltage may then be selected from the two sets respectively to form a combination of high and low energy scanning voltages, which may allow for generating multiple applicable combinations of high and low energy scanning voltages.

It should be noted that, in each of the combinations, a high energy scanning voltage is greater than a low energy scanning voltage.

As for the definition of image quality, the present example makes no limitation on quality specifically and the image quality may be defined according to practical needs. For example, noise may be selected as criterion for defining the image quality.

As an example, an image quality may be determined according to a relative value of noise or an absolute value of noise. If an absolute value of noise is chosen as the selection criterion, then the noise of a CT scanned image may be lower than a preset threshold. In such a case, a set of scanning conditions and a to-be-scanned subject may be preset, and then an absolute value of noise of a CT scanned image of a scanned subject may be measured.

For example, Table 6 illustrates absolute values of noise measured under different scanning conditions with respect to water phantom of different sizes.

TABLE 6

| Absolute values of noise | | | | | | |
|---|---|---|---|---|---|---|
| Noise | 12 inch | 10 inch | 8 inch | 7 inch | 6 inch | 5 inch |
| 80 kv | 14.49 | 8.54 | 4.913 | 3.847 | 2.85 | 2.235 |
| 100 kv | 14.024 | 8.599 | 5.18 | 3.966 | 3.042 | 2.349 |
| 120 kv | 13.811 | 8.564 | 5.215 | 4.087 | 3.17 | 2.447 |
| 140 kv | 13.805 | 8.72 | 5.359 | 4.264 | 3.282 | 2.597 |

Based on Table 6, absolute values of noise under different scanning voltages may be normalized with respect to an absolute value of noise under a scanning voltage of 120 kV, that is, setting an absolute value of noise under a scanning voltage of 120 kV as 1, and then dividing the absolute values of noise under other scanning voltages by the absolute value of noise under a scanning voltage of 120 kV in order to obtain normalized absolute values of noise as shown in Table 7.

TABLE 7

Normalized absolute values of noise

| Noise  | 12 inch | 10 inch | 8 inch | 7 inch | 6 inch | 5 inch |
|--------|---------|---------|--------|--------|--------|--------|
| 80 kv  | 1.0492  | 0.9972  | 0.9421 | 0.9413 | 0.8991 | 0.9134 |
| 100 kv | 1.0154  | 1.0041  | 0.9933 | 0.9704 | 0.9596 | 0.9600 |
| 120 kv | 1.0000  | 1.0000  | 1.0000 | 1.0000 | 1.0000 | 1.0000 |
| 140 kv | 0.9996  | 1.0182  | 1.0276 | 1.0433 | 1.0353 | 1.0613 |

The noises of water phantoms of different sizes under different scanning voltages as shown in Table 7, are recorded as Noise (kv, D), where, kv represents a scanning voltage, and D represents the diameter of a water phantom.

If the relative value of noise is chosen as the selection criterion, the ratio of noise in a CT scanned image with respect to the noise of a reference image is lower than a reference value preset by a user. A reference image noise may be an image noise value according to a scanning protocol of default settings. The relative value of noise may be calculated as follows:

$$Noise_{target} = NoiseLevel * Noise_{ref}$$

where, $Noise_{ref}$ represents the reference noise, $Noise_{target}$ represents the target noise, $Noise_{ref}$ and $Noise_{target}$ both represent absolute values of noise, and NoiseLevel represents the relative ratio between a target noise and the reference noise, and may be a relative value of noise.

For example, by setting scanning conditions including different scanning voltages and tube currents (mAs, current*time) and same CT Dose Index (CTDI), and by collecting data about water phantoms of different sizes, multiple absolute values of noise may be acquired.

Specific scanning conditions may be configured as follows:
CTDI=13.5 mGy;
80 kv, 800 mAs; 100 kv, 342 mAs; 120 kv, 94 mAs; 140 kv, 128 mAs.

The following may provide an example illustrating how to generate a set of low energy scanning voltages and a set of high energy scanning voltages by using a relative value of noise as the selection criterion for determining an image quality.

Take the low energy scanning voltages as an example. When generating a set of low energy scanning voltages, first, a target level (NoiseLevel1) for the relative values of noise is set, and a scanning dose required for the relative value of noise with respect to each of all the scanning voltages supported by a CT system may be sequentially calculated.

If the CT system is able to support a scanning dose under a current scanning voltage, then a scanning voltage corresponding to a scanning dose may then be added into the set of low energy scanning voltages. Otherwise, if a CT system cannot support a scanning dose under a current scanning voltage, a scanning voltage corresponding to the scanning dose may not be added. In this way, a set of low energy scanning voltages $T_{kv\_low}$ may be generated, as shown in Table 8.

For high energy scanning voltages, a target level of the relative values of noise (NoiseLevel2) may then be set. Then in a similar way, a set of high energy scanning voltages $T_{kv\_high}$ may be generated, as shown in Table 9.

A target level for high energy scanning voltages (NoiseLevel2) may be the same as or different from a target level (NoiseLevel1) for the low energy scanning voltages.

TABLE 8

A set of low energy scanning voltages

| $KV_{l1}$  | $KV_{l2}$  | ... | $KV_{li}$  | ... |
|------------|------------|-----|------------|-----|
| $mAs_{l1}$ | $mAs_{l2}$ | ... | $mAs_{li}$ | ... |

TABLE 9

A set of high energy scanning voltages

| $KV_{h1}$  | $KV_{h2}$  | ... | $KV_{hi}$  | ... |
|------------|------------|-----|------------|-----|
| $mAs_{h1}$ | $mAs_{h2}$ | ... | $mAs_{hi}$ | ... |

A scanning dose required by the relative value of noise may then be calculated as follows:

$$mAs_{target} = \frac{NoiseLevel}{1/Noise(kv,D)} * mAs_{ref} * pow\left(\frac{\exp(-\mu_{water} * D_{ref})}{\exp(-\mu_{water} * D_{scan})}, adjCoef\right) \quad (1)$$

where, NoiseLevel represents the target level of the relative value of noise;

Noise(kv,D) represents noise under different scanning voltages with respect to water phantoms of different sizes;

$mAs_{ref}$ references a scanning dose of scanning protocol of default settings with which a reference noise can be obtained during scanning;

$mAs_{target}$ represents target scanning dose obtained through calculation by which a target noise may be obtained during scanning;

$D_{ref}$ represents a default diameter of equivalent water phantom specified in scanning protocol of default settings;

$D_{scan}$ represents an attenuation diameter of equivalent water phantom of a scanned subject;

adjCoef represents an adjusting coefficient of dose calculation, selected from a range of 0-1, and may be selected as 0.5 by default;

$\mu_{water}$ represents the attenuation coefficient of water.

Generally, a slice of a human body may comprise approximately an oval shape and the distribution and configurations of tissues may be rather complicated. In order to simplify the complexity of calculation in the above process, a slice of a human body is equalised as a round slice and all the human tissues may be equalised as water, where this equivalent model may be referred to as an "equivalent water phantom."

In plain film scanning, when calculating the diameter of an equivalent water phantom of a region to be scanned, the method may involve: first, dividing the region to be scanned into a plurality of slices, and calculating the diameter of an equivalent water phantom with respect to each of the divided slices, and then, based on the diameter of the equivalent water phantom of each of the divided slices, calculating the diameter of an equivalent water phantom of an overall region to be scanned.

Usually, in order to acquire the diameter of an equivalent water phantom of an overall region to be scanned based on the diameter of an equivalent water phantom of each of the divided slices, an "average method" or a "maximum method" may be adopted. The average method may refer to calculating an average value of the diameter of an equivalent water phantom of each of the divided slices and using it as the diameter of an equivalent water phantom of the overall region. The maximum method may be used to first sort the diameter of an equivalent water phantom of each of the divided slices in a certain order, then to calculate the average value of the relatively large diameters selected in a proper proportion, which may usually be 5%-50%, and finally to use the average value as the diameter of an equivalent water phantom of an overall region to be scanned.

For a specific slice, the diameter of an equivalent water phantom may be calculated as follows:

Firstly, acquiring plain film raw data of the slice, which may be collected through N detecting channels, for example, rawdata=$\{\mu_0 l_0, \mu_1 l_1, \ldots, \mu_i l_i\}, i=0,1,2,3,\ldots,N-1$.

Then, calculating a total attenuation area of the slice based on the plain film raw data.

The total attenuation area may be defined in some examples as follows:

$$S = \sum_{i=0}^{N-1} (\mu_i l_i + \mu_{i+1} l_{i+1}) * \Delta/2, \text{ where } \Delta = R * \left(\frac{\alpha}{N}\right).$$

Finally, based on a total attenuation area of the slice, calculating the attenuation diameter $D_{scan}$ of an equivalent water phantom of the slice may be performed as follows:

$D_{scan}=2*\text{sqrt}(\text{mean}(S)/(PI*\mu_{water}))$;

where, N represents the number of the channels;

$\mu_i$ represents the average attenuation coefficient of the subject on the $i^{th}$ channel;

$l_i$ represents the length of the path of the subject on the $i^{th}$ channel;

$\Delta$ represents the distance between adjacent detectors;

R represents the radius of rotation;

$\alpha$ represents the sector angle of detector;

mean (s) represents an average of the attenuation areas of all the plain film slices in the Z direction.

Further, available scanning voltages may then selected from a set of low energy scanning voltages $T_{kv\_low}$ and a set of high energy scanning voltages $T_{kv\_high}$ to form multiple combinations of high and low energy scanning voltages. According to an example, all the scanning voltages in the two sets may be sequentially searched to generate available combinations of high and low energy scanning voltages, as shown in Table 10.

TABLE 10

Available combinations of high and low energy scanning voltages

| $KV_{l1}/KV_{h1}$ | | $KV_{l1}/KV_{h2}$ | | ... | $KV_{li}/KV_{hj}$ | ... |
|---|---|---|---|---|---|---|
| $KV_{l1}$ | $KV_{h1}$ | $KV_{l1}$ | $KV_{h2}$ | ... $KV_{li}$ | $KV_{hj}$ | ... |
| $mAs_{l1}$ | $mAs_{h1}$ | $mAs_{l1}$ | $mAs_{h2}$ | ... $mAs_{li}$ | $mAs_{hj}$ | ... |

An example will be described below illustrating a process of selecting an optimal combination of high and low energy scanning voltages from all the generated combinations of scanning voltages based on a specific criterion of selection.

For example, the degree of contrast of a to-be-scanned material may be used as the criterion of selection. Suppose that a user sets the criterion of selection as a $DE_{contrast}$ of material cort bone in Table 3 and iodine concentration 4, and further suppose that all the scanning voltages supported by a CT system are selected from 80 kV/100 kV/120 kV/140 kV. Therefore, available combinations of high and low energy scanning voltages may be obtained by querying Table 10. Further, a $DE_{ratio}$ corresponding to each of the available combinations may be determined according to Table 3 and Table 4. Thus, a corresponding $DE_{contrast}$ may be calculated. Then, if a $DE_{contrast}$ is larger than a preset threshold, the corresponding combination of high and low energy scanning voltages may be selected as a candidate combination. Similarly, all the candidate combinations may be determined. A candidate combination having the greatest absolute value of $DE_{contrast}$ may be selected as an optimal combination of high and low energy scanning voltages.

When taking the degree of contrast of a to-be-scanned material with a constraint of noise index as the criterion of selection, or taking the degree of contrast of a to-be-scanned material with constraints of noise and dose as the criterion of selection, the calculation and selection process may be similar to the above described process of using the degree of contrast of a to-be-scanned material as the criterion of selection, except that $DE_{contrast}$ may be replaced with $DE_{CNR}$ and $DE_{CNDR}$, respectively.

When taking the degree of contrast of spectrums of high and low energy scanning voltages as the criterion of selection, the process may include sequentially searching all the combinations of high and low energy scanning voltages supported by the system from Table 10, calculating an overlapping area $DE_{Area}$ of the spectrum of a low energy scanning voltage and the spectrum of a high energy scanning voltage corresponding to each of the combinations, and from the set of the combinations of high and low energy scanning voltages $T\{DE_{Area}\}$ each of which may have a $DE_{Area}$ greater than a preset threshold, selecting a combination corresponding to the minimum $DE_{Area}$ as an optimal combination of high and low energy scanning voltages.

When taking the degree of contrast of spectrums of high and low energy scanning voltages with a constraint of dose as the criterion of selection, the selection and calculation process may be based on a process of using the degree of contrast of spectrums of high and low energy scanning voltages as the criterion of selection. The difference may be from the set of the combinations $T\{DE_{Area}\}$ each of which has a $DE_{Area}$ greater than a pre-set threshold, to select the combination corresponding to the minimum scanning dose as the optimal combination of high and low energy scanning voltages.

In the present disclosure, the methods may preset a criterion of selection and select an optimal combination of high and low energy scanning voltages that satisfy a preset criterion of selection. Thus, the present disclosure may provide a variety of choices with respect to selection criterion and may further provide a wide range of applications.

Figure 3:
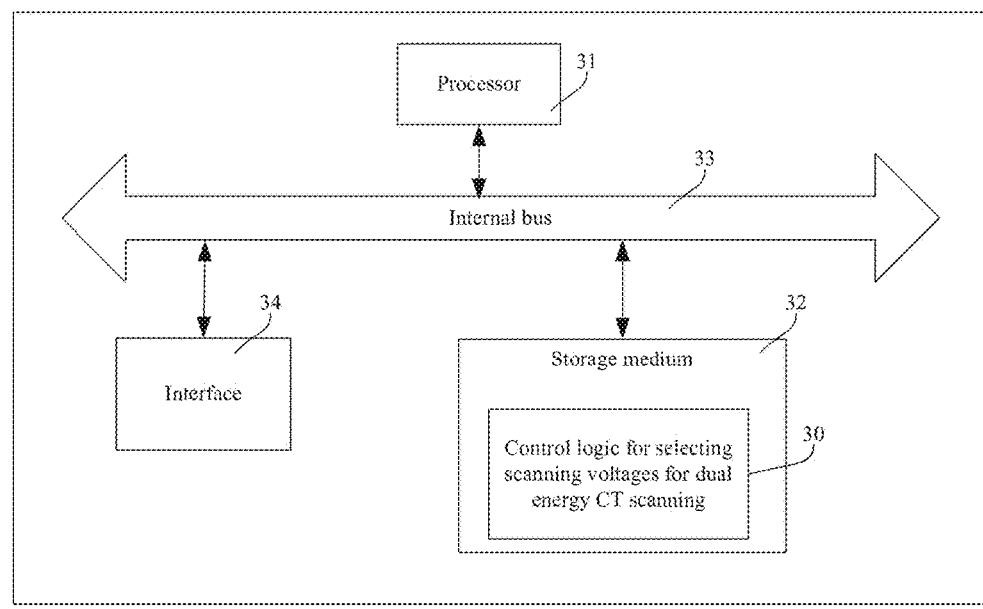
FIG. 3 is a schematic graph illustrating hardware architecture of an apparatus for selecting scanning voltages for dual energy CT scanning according to an example of the present disclosure.

The present disclosure may also provide an apparatus for selecting high and low energy scanning voltages for dual energy CT scanning. Referring to FIG. 3, the apparatus includes a processor 31 such as central processing unit (CPU) and a machine-readable storage medium 32 connected with the processor 31 through an internal bus 33. In other possible implementations, the apparatus may also include an external interface 34 so as to allow the apparatus to communicate with other components, devices or apparatuses.

In different examples, the machine readable storage medium 32 may include: Random Access Memory (RAM), volatile memory, non-volatile memory, flash memory, memory drive (such as hard disk drive), solid state hard disk, other types of storage disk (such as optical disc or dvd), or similar types of storage medium or combinations thereof.

Figure 4:
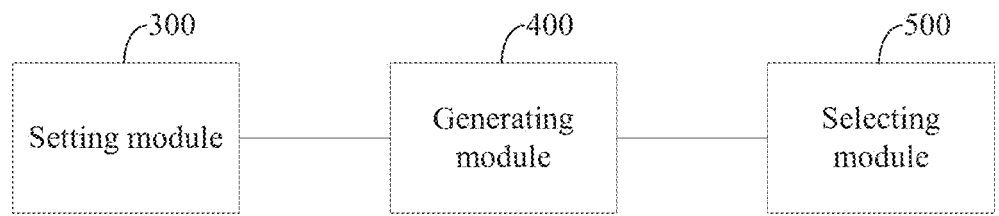
FIG. 4 is a block diagram illustrating functional blocks of a control logic for selecting scanning voltages for dual energy CT scanning according to an example of the present disclosure.

Further, the machine-readable storage medium 32 may store machine-readable instructions corresponding to control logic 30 for selecting high and low energy scanning voltages. In terms of functionality, as shown in FIG. 4, the control logic 30 may mainly include a setting module 300, a generating module 400 and a selecting module 500.

A setting module 300 may be configured to set a criterion of selection for high and low energy scanning voltages.

In practice, the criterion of selection may be selected in a flexible way according to the model of the CT scanner system, and application scenario, etc. For example, the criterion of selection may be any one selected from the following: the degree of contrast of a to-be-scanned material, the degree of contrast of a to-be-scanned material with a constraint of noise index, the degree of contrast of a to-be-scanned material with constraints of noise and dose, the degree of contrast of spectrums of high and low energy scanning voltages, or the degree of contrast of spectrums of high and low energy scanning voltages with a constraint of dose.

A generating module 400 may be configured to generate combinations of high and low energy scanning voltages from the scanning voltages supported by a CT scanner system, each of the combinations including a high energy scanning voltage and a low energy scanning voltage.

For example, a set of low energy scanning voltages and a set of high energy scanning voltages may be generated each of which may satisfy the image quality. A low energy scanning voltage and a high energy scanning voltage may then be selected from the respective set of the two sets to form a combination of high and low energy scanning voltages. The above mentioned image quality may be determined by a user based on practical needs and the present disclosure makes no definition on it.

A selecting module 500 may be configured to select an optimal combination of high and low energy scanning voltages from all the available combinations of high and low energy scanning voltages.

Figure 5:
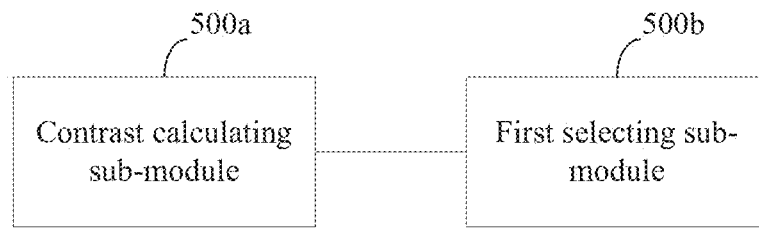
FIG. 5 is a block diagram illustrating functional blocks of a control logic for selecting scanning voltages for dual energy CT scanning based on degree of contrast of a to-be-scanned material according to an example of the present disclosure.

Further, as shown in FIG. 5, when taking the degree of contrast of a to-be-scanned material as the criterion of selection, the selecting module 500 may include a contrast calculating sub-module 500a and a first selecting sub-module 500b.

The contrast calculating sub-module 500a may be configured to calculate the degree of contrast $DE_{contrast}$ of a to-be-scanned material, specifically as follows:

$$DE_{contrast} = DE_{ratio\_material1} - DE_{ratio\_material2};$$

$$DE_{ratio} = \frac{CT_{highKV} - CT_{highKV\_ref}}{CT_{lowKV} - CT_{lowKV\_ref}};$$

where, $DE_{ratio}$ represents a ratio of CT values of high and low energy scanning voltages of a to-be-scanned material (referred to as "a high/low ratio of a to-be-scanned material");

$DE_{ratio\_material1}$ represents the high/low ratio of a first to-be-scanned material;

$DE_{ratio\_material2}$ represents the high/low ratio of a second to-be-scanned material;

$CT_{lowKV\_ref}$ and $CT_{highKV}$ represent the CT values of a to-be-scanned material under a low energy scanning voltage and a high energy scanning voltage respectively;

$CT_{lowKV\_ref}$ represents the CT value of a preset reference material under a low energy scanning voltage;

$CT_{highKV\_ref}$ represents the CT value of the reference material under a high energy scanning voltage;

$DE_{ratio}$ may be acquired through experiments or calculations in advance.

The first selecting sub-module 500b may be configured to select a combination of high and low energy scanning voltages corresponding to the greatest absolute value of the degree of contrast $DE_{contrast}$ of a to-be-scanned material as an optimal combination of high and low energy scanning voltages.

Table 1-Table 5 may be referred to for the details of the calculation.

Figure 6:
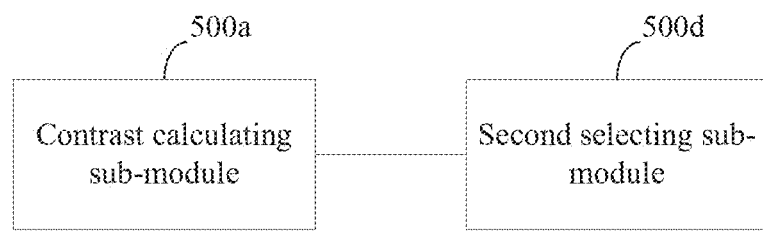
FIG. 6 is a block diagram illustrating functional blocks of a control logic for selecting scanning voltages for dual energy CT scanning based on degree of contrast of a to-be-scanned material with constraint of noise index according to an example of the present disclosure.

Further, referring to FIG. 6, when taking the degree of contrast of a to-be-scanned material with a constraint of noise index as the criterion of selection, the selecting module 500 may include the contrast calculating sub-module 500a and a second selecting sub-module 500d.

The second selecting sub-module 500d may be configured to select the combination of high and low energy scanning voltages corresponding to the greatest absolute value of the degree of contrast of a to-be-scanned material with a constraint of noise index $DE_{CNR}$, as an optimal combination of high and low energy scanning voltages, where, $DE_{CNR}$ may be calculated using the following equation:

$$DE_{CNR} = \frac{DE_{contrast}}{Noise};$$

where, Noise represents a known quantity, which may be a preset noise index.

Figure 7:
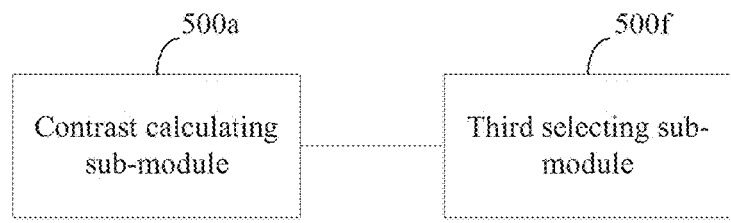
FIG. 7 is a block diagram illustrating functional blocks of a control logic for selecting scanning voltages for dual energy CT scanning based on degree of contrast of a to-be-scanned dual energy material with constraint of noise and dose according to an example of the present disclosure.

Further, referring to FIG. 7, when taking the degree of contrast of a to-be-scanned material with constraint of noise and dose as the criterion of selection, the selecting module 500 may include the contrast calculating sub-module 500a and a third selecting sub-module 500f.

The third selecting sub-module 500f may be configured to select a combination of high and low energy scanning voltages corresponding to the greatest absolute value of the degree of contrast of a to-be-scanned material with constraint of noise and dose $DE_{CNRD}$, as an optimal combination of high and low energy scanning voltages where, $DE_{CNRD}$ may be calculated using the following equation:

$$DE_{CNRD} = \frac{DE_{contrast}}{Noise * CTDI};$$

where, CTDI represents the sum of the scanning dose corresponding to a high energy scanning voltage and the scanning dose corresponding to a low energy scanning voltage, which may be calculated in advance; Noise may be a known quantity, which may be a preset noise index.

Figure 8:
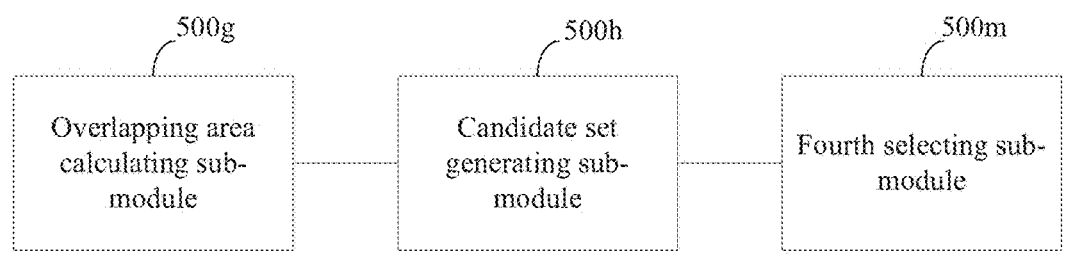
FIG. 8 is a block diagram illustrating functional blocks of a control logic for selecting scanning voltages of dual energy CT scanning based on degree of contrast of spectrums of dual energy scanning voltages according to an example of the present disclosure.

Further, referring to FIG. 8, when taking the degree of contrast of the spectrums of high and low energy scanning voltages as the criterion of selection, the selecting module 500 may include an overlapping area calculating sub-module 500g, a candidate set generating sub-module 500h and a fourth selecting sub-module 500m.

The overlapping area calculating sub-module 500g may be configured to calculate an overlapping area $DE_{Area}$ of a spectrum corresponding to a low energy scanning voltage and a spectrum corresponding to a high energy scanning voltage in each of the combinations of high and low energy scanning voltages.

The candidate set generating sub-module 500*h* may be configured to generate a set of the combinations of high and low energy scanning voltages each of which may comprise an overlapping area less than a pre-set value, used as a candidate set.

The fourth selecting sub-module 500*m* may be configured to select the combination of high and low energy scanning voltages corresponding to a minimum overlapping area from the candidate set as an optimal combination of high and low energy scanning voltages.

Figure 9:
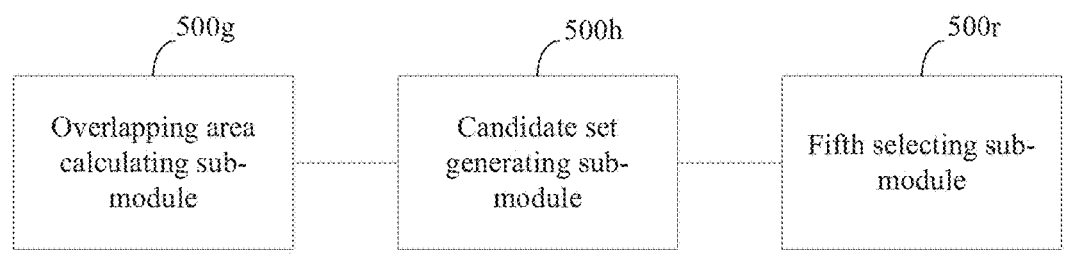
FIG. 9 is a block diagram illustrating functional blocks of a control logic for selecting scanning voltages of dual energy CT scanning based on degree of contrast of spectrums of dual energy scanning voltages with a constraint of dose according to an example of the present disclosure.

Further, referring to FIG. 9, when taking the degree of contrast of the spectrums of high and low energy scanning voltages with a constraint of dose as the criterion of selection, the selecting module 500 may include an overlapping area calculating sub-module 500*g*, the candidate set generating sub-module 500*h* and a fifth selecting sub-module 500*r*.

The fifth selecting sub-module 500*r* may be configured to select the combination of high and low energy scanning voltages corresponding to a minimum scanning dose from a candidate set as an optimal combination of high and low energy scanning voltages.

The following is an example of a software implementation further illustrating how the apparatus may execute the control logic 30 for selecting high and low energy scanning voltages for dual energy CT scanning. In this example, the control logic 30 should be understood as computer-readable instructions stored in the machine-readable storage medium 32. When the processor 31 on the apparatus executes the control logic 30, the processor 31 may execute the instructions of corresponding functional modules of the control logic 30 stored on the machine-readable storage medium 32 to:

set a criterion of selection for selecting high and low energy scanning voltages for a dual energy CT scanner;

generate combinations of high and low energy scanning voltages according to the scanning voltages supported by the dual energy CT scanner, wherein each of the combinations includes a high energy scanning voltage and a low energy scanning voltage;

select a combination of high and low energy scanning voltages from the generated combinations based on the criterion of selection.

The criterion of selection may include:
the degree of contrast of a to-be-scanned material;
the degree of contrast of a to-be-scanned material with constraint of noise index;
the degree of contrast of a to-be-scanned material with constraint of noise and dose;
the degree of contrast of the spectrum corresponding to a high energy scanning voltage and the spectrum corresponding to a low energy scanning voltage; and
the degree of contrast of the spectrum corresponding to a high energy scanning voltage and the spectrum corresponding to a low energy scanning voltage with constraint of dose.

Further, according to an example, when taking the degree of contrast of a to-be-scanned material as a criterion of selection, the instructions may further cause the processor to:

select a combination of high and low energy scanning voltages corresponding to the greatest absolute value of a degree of contrast of a to-be-scanned material $DE_{contrast}$;

$$DE_{contrast} = DE_{ratio\_material1} - DE_{ratio\_material2};$$

$$DE_{ratio} = \frac{CT_{highKV} - CT_{highKV\_ref}}{CT_{lowKV} - CT_{lowKV\_ref}};$$

wherein, $DE_{ratio}$ represents a high/low ratio of a to-be-scanned material (the ratio of the CT values of high and low energy scanning voltages of a to-be-scanned material);

$DE_{ratio\_material1}$ represents the high/low ratio of a first to-be-scanned material;

$DE_{ratio\_material2}$ represents the high/low ratio of a second to-be-scanned material;

$CT_{lowKV}$ and $CT_{highKV}$ represent the CT value of a to-be-scanned material corresponding to a low energy scanning voltage and the CT value of a to-be-scanned material corresponding to a high energy scanning voltage;

$CT_{lowKV\_ref}$ represents a CT value of a preset reference material under a low energy scanning voltage;

$CT_{highKV\_ref}$ represents a CT value of a reference material under a high energy scanning voltage;

$DE_{ratio}$ may be acquired through experiments and calculation in advance.

Further, according to an example, when taking the degree of contrast of a to-be-scanned material with a constraint of noise index as the criterion of selection, the instructions may further cause the processor to:

select the combination of high and low energy scanning voltages corresponding to the greatest absolute value of the degree of contrast of the to-be-scanned material with constraint of noise index $DE_{CNR}$;

the degree of contrast of the to-be-scanned material with constraint of noise index $DE_{CNR}$ may be calculated as follows:

$$DE_{CNR} = \frac{DE_{contrast}}{Noise};$$

wherein, Noise represents a known quantity, which may be a preset noise index;

$DE_{contrast}$ represents the degree of contrast of the to-be-scanned material.

Further, according to an example, when taking the degree of contrast of the to-be-scanned material with constraints of noise and dose as the criterion of selection, the instructions may further cause the processor to:

select the combination of high and low energy scanning voltages corresponding to the greatest absolute value of the degree of contrast of the to-be-scanned material with constraints of noise and dose $DE_{CNRD}$;

wherein, the degree of contrast of the to-be-scanned material with constraint of noise and dose $DE_{CNRD}$ may be calculated as follows:

$$DE_{CNRD} = \frac{DE_{contrast}}{Noise * CTDI};$$

wherein, CTDI represents the sum of the scanning dose corresponding to the high energy scanning voltage and the scanning dose corresponding to the low energy scanning voltage, which is calculated in advance;

Noise represents a known quantity, which may be a preset noise index.

Further, according to an example, when taking the degree of contrast of the spectrums of high and low energy scanning voltages as the criterion of selection, the instructions may further cause the processor to:

acquire an overlapping area $DE_{Area}$ of the spectrum corresponding to the low energy scanning voltage and the spectrum corresponding to the high energy scanning voltage in each of the combinations of high and low energy scanning voltages;

select all the combinations each of which may comprise an overlapping area less than a preset value to form a candidate set;

select a combination corresponding to the minimum overlapping area from a candidate set.

Further, according to an example, when taking the degree of contrast of the spectrums of high and low energy scanning voltages with constraint of dose as the criterion of selection, the instructions may further cause the processor to:

acquire an overlapping area $DE_{Area}$ of the spectrum corresponding to the low energy scanning voltage and the spectrum corresponding to the high energy scanning voltage in each of the combinations of high and low energy scanning voltages;

select all the combinations of high and low energy scanning voltages each of which may comprise an overlapping area less than a pre-set value to form a candidate set; and select a combination of high and low energy scanning voltages corresponding to the minimum scanning dose from a candidate set.

Further, in order to generate combinations of high and low energy scanning voltages based on the scanning voltages supported by the CT device, according to an example, the instructions may further cause the processor to:

divide all the scanning voltages supported by a CT device and satisfying an image quality into a set of low energy scanning voltages and a set of high energy scanning voltages;

select a low energy scanning voltage and a high energy scanning voltage from the set of low energy scanning voltages and the set of high energy scanning voltages respectively to form a combination of high and low energy scanning voltages.

The image quality may be determined using an absolute value of noise or to relative value of noise as the criterion.

The above are only preferred examples of the present disclosure and are not intended to limit the disclosure within its spirit and/or principles. Any changes made, equivalent replacements, or improvement in the protection of the present disclosure should contain within its range.

The methods, processes and units described herein may be implemented by hardware (including hardware logic circuitry), software or firmware or a combination thereof. The term 'processor' is to be interpreted broadly to include a processing unit, ASIC, logic unit, or programmable gate array etc. The processes, methods and functional units may all be performed by the one or more processors; reference in this disclosure or the claims to a 'processor' should thus be interpreted to mean 'one or more processors'.

Further, the processes, methods and functional units described in this disclosure may be implemented in the form of a computer software product. The computer software product may be stored in a storage medium and may comprise a plurality of instructions for making a processor implement the methods recited in the examples of the present disclosure.

The figures are only illustrations of an example, wherein the units or procedure shown in the figures may not necessarily be essential for implementing the present disclosure. Those skilled in the art will understand that the units in the device in the example may be arranged in the device in the examples as described, or may be alternatively located in one or more devices different from that in the examples. The units in the examples described may be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

Throughout the present disclosure, the word "comprise", or variations such as "comprises" or "comprising", will be understood to imply the inclusion of a stated element, integer or step, or set of elements, integers or steps, but not the exclusion of any other element, integer or step, or set of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method for selecting high and low energy scanning voltages for a dual energy CT scanner, the method comprising:

setting a criterion of selection for selecting the high and low energy scanning voltages based on a degree of contrast of a to-be-scanned material;

wherein the degree of contrast of the to-be-scanned material, $DE_{contrast}$, is calculated as follows:

$$DE_{contrast} = DE_{ratio\_material1} - DE_{ratio\_material2};$$

$$DE_{ratio} = \frac{CT_{highKV} - CT_{highKV\_ref}}{CT_{lowKV} - CT_{lowKV\_ref}};$$

wherein $DE_{ratio}$ represents a ratio of CT values of high and low energy scanning voltages of the to-be-scanned material ("a high/low ratio"), $DE_{ratio\_material1}$ represents a high/low ratio of a first to-be-scanned material, $DE_{ratio\_material2}$ represents a high/low ratio of a second to-be-scanned material, $CT_{lowKV}$ and $CT_{highKV}$ represent a CT value of the to-be-scanned material under a low energy scanning voltage and a CT value of the to-be-scanned material under a high energy scanning voltage, $CT_{lowKV\_ref}$ represents a CT value of a preset reference material under a low energy scanning voltage, $CT_{highKV\_ref}$ represents a CT value of the preset reference material under a high energy scanning voltage, and $DE_{ratio}$ is acquired through experiments or calculations in advance;

generating combinations of high and low energy scanning voltages according to all scanning voltages supported by the dual energy CT scanner, wherein each of the combinations comprises a high energy scanning voltage and a low energy scanning voltage; and selecting a combination of high and low energy scanning voltages from the generated combinations of high and low energy scanning voltages based on the criterion of selection.

2. The method of claim 1, wherein selecting the combination of high and low energy scanning voltages comprises:

selecting a combination corresponding to the greatest absolute value of the degree of contrast of the to-be-scanned material $DE_{contrast}$.

3. The method of claim 1, wherein the degree of contrast of the to-be-scanned material has constraint of noise index, and selecting the combination of high and low energy scanning voltages comprises:

selecting a combination of high and low energy scanning voltages corresponding to the greatest absolute value of the degree of contrast of the to-be-scanned material having constraint of noise index $DE_{CNR}$;

wherein the degree of contrast of the to-be-scanned material having constraint of noise index $DE_{CNR}$ is calculated as follows:

$$DE_{CNR} = \frac{DE_{contrast}}{\text{Noise}};$$

wherein

Noise is a known quantity, which is a preset noise index, and $DE_{contrast}$ represents the degree of contrast of the to-be-scanned material.

4. The method of claim 1, wherein the degree of contrast of the to-be-scanned material has constraint of noise and dose, and selecting the combination of high and low energy scanning voltages comprises:

selecting a combination of high and low energy scanning voltages corresponding to the greatest absolute value of the degree of contrast of the to-be-scanned material having constraint of noise and dose $DE_{CNRD}$;

wherein the degree of contrast of the to-be-scanned material having constraint of noise and index $DE_{CNRD}$ is calculated as follows:

$$DE_{CNRD} = \frac{DE_{contrast}}{\text{Noise} * CTDI};$$

wherein

CTDI represents a sum of a scanning dose corresponding to a high energy scanning voltage and a scanning dose corresponding to a low energy scanning voltage, which is calculated in advance, Noise is a known quantity, which is a preset noise index, and $DE_{contrast}$ represents the degree of contrast of the to-be-scanned material.

5. The method of claim 1, wherein generating the combinations of high and low energy scanning voltages according to all scanning voltages supported by the dual energy CT scanner comprises:

dividing all scanning voltages supported by the dual energy CT scanner and satisfying an image quality into a set of low energy scanning voltages and a set of high energy scanning voltages; and selecting a low energy scanning voltage and a high energy scanning voltage from the set of low energy scanning voltages and the set of high energy scanning voltages respectively to form a combination of high and low energy scanning voltages.

6. The method of claim 5, wherein the image quality is determined based on a relative value of noise or an absolute value of noise.

7. The method of claim 1, wherein the method is performed by an apparatus for selecting high and low energy scanning voltages for the dual energy CT scanner, the apparatus comprising:

a processor which invokes machine readable instructions corresponding to a control logic for selecting high and low energy scanning voltages stored on a non-transitory storage medium and executes the machine readable instructions to:

perform the method for selecting the high and low energy scanning voltages for the dual energy CT scanner.

8. A method for selecting high and low energy scanning voltages for a dual energy CT scanner, the method comprising:

setting a criterion of selection based on a degree of contrast of spectrums of high and low energy scanning voltages;

generating combinations of high and low energy scanning voltages according to all scanning voltages supported by the dual energy CT scanner, wherein each of the combinations of high and low energy scanning voltages comprises a high energy scanning voltage and a low energy scanning voltage; and selecting a combination of high and low energy scanning voltages by:

acquiring an overlapping area $DE_{Area}$ of a spectrum corresponding to a low energy scanning voltage and a spectrum corresponding to a high energy scanning voltage in each of the combinations of high and low energy scanning voltages;

selecting all combinations of high and low energy scanning voltages each of which has an overlapping area less than a preset value to form a candidate set; and selecting a combination of high and low energy scanning voltages corresponding to a minimum overlapping area from the candidate set.

9. The method of claim 8, where the method is performed by an apparatus for selecting high and low energy scanning voltages for the dual energy CT scanner, the apparatus comprising:

a processor which invokes machine readable instructions corresponding to a control logic for selecting high and low energy scanning voltages stored on a non-transitory storage medium and executes the machine readable instructions to perform the method for selecting the high and low energy scanning voltages for the dual energy CT scanner.

10. A method for selecting high and low energy scanning voltages for a dual energy CT scanner, the method comprising:

setting a criterion of selection based on a degree of contrast of spectrums of high and low energy scanning voltages having constraint of dose;

generating combinations of high and low energy scanning voltages according to all scanning voltages supported by the dual energy CT scanner, wherein each of the combinations of high and low energy scanning voltages comprises a high energy scanning voltage and a low energy scanning voltage; and selecting a combination of high and low energy scanning voltages by:

acquiring an overlapping area $DE_{Area}$ of a spectrum corresponding to a low energy scanning voltage and a spectrum corresponding to a high energy scanning voltage in each of the combinations of high and low energy scanning voltages;

selecting all combinations of high and low energy scanning voltages each of which has an overlapping area less than a preset value to form a candidate set; and selecting a combination of high and low energy scanning voltages corresponding to a minimum scanning dose from the candidate set.

11. The method of claim 10, where the method is performed by an apparatus for selecting high and low energy scanning voltages for the dual energy CT scanner, the apparatus comprising:

a processor which invokes machine readable instructions corresponding to a control logic for selecting high and low energy scanning voltages stored on a non-transitory storage medium and executes the machine readable instructions to perform the method for the selecting high and low energy scanning voltages for the dual energy CT scanner.

* * * * *